United States Patent [19]
Cochran et al.

[11] Patent Number: 5,051,825
[45] Date of Patent: Sep. 24, 1991

[54] DUAL IMAGE VIDEO INSPECTION APPARATUS

[75] Inventors: Don W. Cochran, Mayfield Village; James R. Austin, Mentor On the Lake, both of Ohio

[73] Assignee: Pressco, Inc., Solon, Ohio

[21] Appl. No.: 409,148

[22] Filed: Sep. 19, 1989

Related U.S. Application Data

[63] Continuation-in-part of Ser. No. 336,642, Apr. 7, 1989, Pat. No. 4,882,498, which is a continuation-in-part of Ser. No. 107,265, Oct. 9, 1987, abandoned.

[51] Int. Cl.⁵ .................. H04N 7/18; H04N 7/00
[52] U.S. Cl. ..................... 358/106; 358/10; 358/93; 356/237; 382/8
[58] Field of Search ............ 358/106, 101, 107, 93; 356/237; 382/8; 250/571, 723 B

[56] References Cited

U.S. PATENT DOCUMENTS

| | | | |
|---|---|---|---|
| 3,222,524 | 12/1965 | Lee | 250/106 |
| 3,746,784 | 7/1973 | Van Oosterhout | 358/106 |
| 3,903,416 | 9/1975 | Fox | 250/360 |
| 4,002,823 | 1/1977 | Van Oosterhout | 358/106 |
| 4,141,566 | 11/1978 | Peyton et al. | 358/101 |
| 4,165,277 | 8/1979 | Frewin | 209/3.3 |
| 4,217,491 | 8/1980 | Dufford, Jr. et al. | 250/223 R |
| 4,256,957 | 3/1981 | Ford et al. | 250/223 B |
| 4,271,408 | 6/1981 | Teshima et al. | 340/702 |
| 4,293,219 | 10/1981 | Ducloux | 356/240 |
| 4,305,658 | 12/1981 | Yoshida | 356/23 |
| 4,318,808 | 3/1982 | Atkinson | 209/533 |
| 4,343,021 | 8/1982 | Frame | 358/213 |
| 4,344,146 | 8/1982 | Davis, Jr. et al. | 364/522 |
| 4,349,788 | 3/1984 | Frame | 358/213 |
| 4,364,088 | 12/1982 | Kubota | 358/106 |
| 4,367,405 | 1/1983 | Ford | 250/223 |
| 4,380,025 | 4/1983 | Deane | 358/106 |
| 4,385,233 | 5/1983 | Lovalenti | 250/223 |
| 4,385,318 | 5/1983 | Miller | 358/106 |
| 4,427,800 | 1/1984 | Kanade et al. | 250/222.1 |
| 4,442,455 | 4/1984 | Huignard et al. | 358/209 |
| 4,446,481 | 5/1984 | Edamatsu et al. | 358/106 |
| 4,486,776 | 12/1984 | Yoshida | 358/106 |
| 4,491,868 | 1/1985 | Berridge, Jr. et al. | 358/139 |
| 4,509,076 | 4/1985 | Yoshida | 358/106 |
| 4,530,036 | 7/1985 | Conti | 362/32 |

(List continued on next page.)

FOREIGN PATENT DOCUMENTS 341806 2/1989 European Pat. Off. .
336563 3/1989 European Pat. Off. .

OTHER PUBLICATIONS

Strobe Head for Zapata Industries, Inc. Crown Inspection System.
VideoTek Plastic Closure System Inspection System.
A. Novini, "Fundamentals of Machine Vision Lighting", Penn Video Inc., Copyright 1985.
Penn Video Inc., "Pulsar Machine Vision Strobes".
A. Novini, "Fundamentals of Machine Vision Component Selection", Penn Video Inc. Copyright 1984.
Penn Video Inc. "Programmable Logic Controlled Vision".
A. Novini, "Fundamentals of Strobe Lighting for Machine Vision", Penn Video Inc., Copyright 1987.
G. Wagner, "Combining X-Ray Imaging and Machine Vision", Penn Video Inc., Copyright 1987.
Vinarub, E. J., et al., "Fiber Optics in Machine Vision", Photonics Spectra (Jun. 1987).
Schreiber, Rita R., "Quality Control with Vision", Vision MVA/SME's Quarterly on Vision Technology, vol. 2, No. 4, (Oct. 1985).

(List continued on next page.)

Primary Examiner—John K. Peng
Attorney, Agent, or Firm—Fay, Sharpe, Beall, Fagan, Minnich & McKee

[57] ABSTRACT

A video inspection system includes first and second video cameras mounted along parallel axes. A lighting array is pulsed, and resultant light is reflected from a specimen to both cameras. Orientation of the specimen is determined in accordance with an image generated from a first camera. This data is used to isolate a selected portion of the specimen for analysis by an image generated from the second camera.

17 Claims, 4 Drawing Sheets

U.S. PATENT DOCUMENTS

| | | | |
|---|---|---|---|
| 4,567,551 | 1/1986 | Choate | 362/398 |
| 4,581,632 | 4/1986 | Davis et al. | 358/106 |
| 4,586,080 | 4/1986 | Hoyt et al. | 358/106 |
| 4,595,289 | 6/1986 | Feldman et al. | 356/237 |
| 4,596,037 | 6/1986 | Bouchard et al. | 382/8 |
| 4,604,648 | 8/1986 | Kley | 358/101 |
| 4,606,625 | 6/1986 | Miyazawa et al. | 356/240 |
| 4,673,973 | 6/1987 | Ledley et al. | 358/93 |
| 4,677,473 | 6/1987 | Okamoto | 358/101 |
| 4,692,943 | 9/1987 | Pietzsch et al. | 358/106 |
| 4,693,608 | 9/1987 | Kitagawa et al. | 358/93 |
| 4,731,649 | 3/1988 | Chang et al. | 358/106 |
| 4,758,084 | 7/1988 | Tokumi et al. | 356/237 |
| 4,764,681 | 8/1988 | Michalski et al. | 250/563 |
| 4,764,969 | 8/1988 | Ohtombe et al. | 358/106 |
| 4,769,698 | 9/1988 | Ledley et al. | 358/93 |
| 4,811,251 | 3/1989 | Minato | 364/552 |
| 4,843,231 | 6/1989 | Caloyannis et al. | 250/223 B |
| 4,860,096 | 8/1989 | Long et al. | 358/101 |
| 4,865,447 | 9/1989 | Shay | 356/240 |

OTHER PUBLICATIONS

George, Robert W., "High Speed Video Inspection of Caps and Closures", Vision '85 Conference Proceedings, pp. 1-55 through 1-70 (Mar. 25-28, 1985).

ordinary skill in the art upon a reading and understanding of the subject specification.

DUAL IMAGE VIDEO INSPECTION APPARATUS

BACKGROUND OF THE INVENTION

This application is continuation-in-part of application Ser. No. 336,642, filed Apr. 7, 1989 now U.S. Pat. No. 4,882,498 which patent in turn is a file-wrapper continuation of U.S. patent application Ser. No. 107,265, filed Oct. 9, 1987, now abandoned, the contents of which are incorporated herein by reference.

This application pertains to the art of video inspection, and more particularly to inspection systems for a sequence of generally uniform articles. The invention is particularly applicable to inspections of container components, and will be described with particular reference thereto, although it will be appreciated that the invention has broader applications, such as in any inspection or machine vision system.

Machine vision systems are obtaining increasing significance in industry to aid in robotic assembly systems, as well as inspection systems for quality control. Such machine vision systems are generally comprised of a lighting system to light a specimen, and a camera for sensing light reflected therefrom. A digitized image is formed from an image received by the camera. Data representative of this image is then made available for use in controlling a robot arm, identifying the specimen, or determining whether the specimen is acceptable to specified standards.

A single image is generally adequate for accomplishing video inspection. Often times, however, one or more isolated areas of a specimen have increased significance. Merely increasing resolution of an entire specimen is impractable. Ultra high resolution images of a specimen, even if technologically feasible, are cost prohibitive. In addition, unnecessary data for non-critical areas would be generated, requiring a penalty in image processing and analysis time, or increased cost for more powerful computing hardware. An exemplary critical area is presented given that beverage containers generally include a pull tab to facilitate opening thereof without the aid of a tool. Such a tab is typically mounted to a central portion of a container lid by a rivet formed from the lid material. The rivet is critical in that any flaw therein may result in the development of a leak, or in a tab which is separated from the can prior to opening of the container.

While the afore-mentioned system is adequate for a substantial number of inspections, it provides no means for additional, detailed inspection of selected areas of a specimen. It is therefore desirable that a system be provided which allows for video inspections, with increased resolution on selected, critical areas of the specimen.

The present invention contemplates a new and improved video inspection system which overcomes all of the above-referred problems, and others, and provides a video inspection system allowing for concurrent inspection of a specimen, as a whole, and selected areas of the specimen which are critical in nature.

THE SUMMARY OF THE INVENTION

In accordance with the present invention, there is provided a video inspection apparatus which includes means for receiving light from an associated specimen. First and second video cameras generate image data from light which is directed thereto. Means is provided for providing a first portion of light received from the associated specimen to the first video camera. A second portion of the light is provided to the second video camera. Image data generated from the first video camera is provided to a data processor. The data processor in turn determines, from the first image data, an approximate location of an area of particular interest of the associated specimen. Alignment data, representative of this location, in turn is provided for generating an image of the area of interest in conjunction with the second video camera.

In accordance with a more limited aspect of the invention, a means is provided for determining acceptability of the specimen in accordance with preselected standards, in conjunction with the first or second image data.

In accordance with a yet more limited aspect of the present invention, a lighting array comprised of solid-state light generating emitting elements is pulsed a single time for each of a sequence of specimens. The light generated from this single pulse provides the light to the first and second video cameras for generating image data.

In accordance with another aspect of the present invention, a method is provided for accomplishing a video inspection using first and second video cameras, data obtained from the first video camera is used for aligning the second video camera on an area of particular interest of an associated specimen.

An advantage of the present invention is the provision of a system for video inspection with increased accuracy and reliability.

Another advantage of the present invention is the provision of a system for high-speed video inspection of a series of specimens.

Yet another advantage of the present invention is the provision of a video inspection system which allows for accurate isolation of selected areas of an object by use of image data acquired from first and second video cameras.

Further advantages will become apparent to one of ordinary skill in the art upon a reading and understanding of the subject specification.

BRIEF DESCRIPTION OF THE DRAWINGS

The invention may take physical form in certain parts, and arrangements of parts, a preferred embodiment of which will be described in detail in this specification, and illustrated in the accompanying drawings which form a part hereof, and wherein.

DETAILED DESCRIPTION OF THE PREFERRED EMBODIMENT

Figure 1:
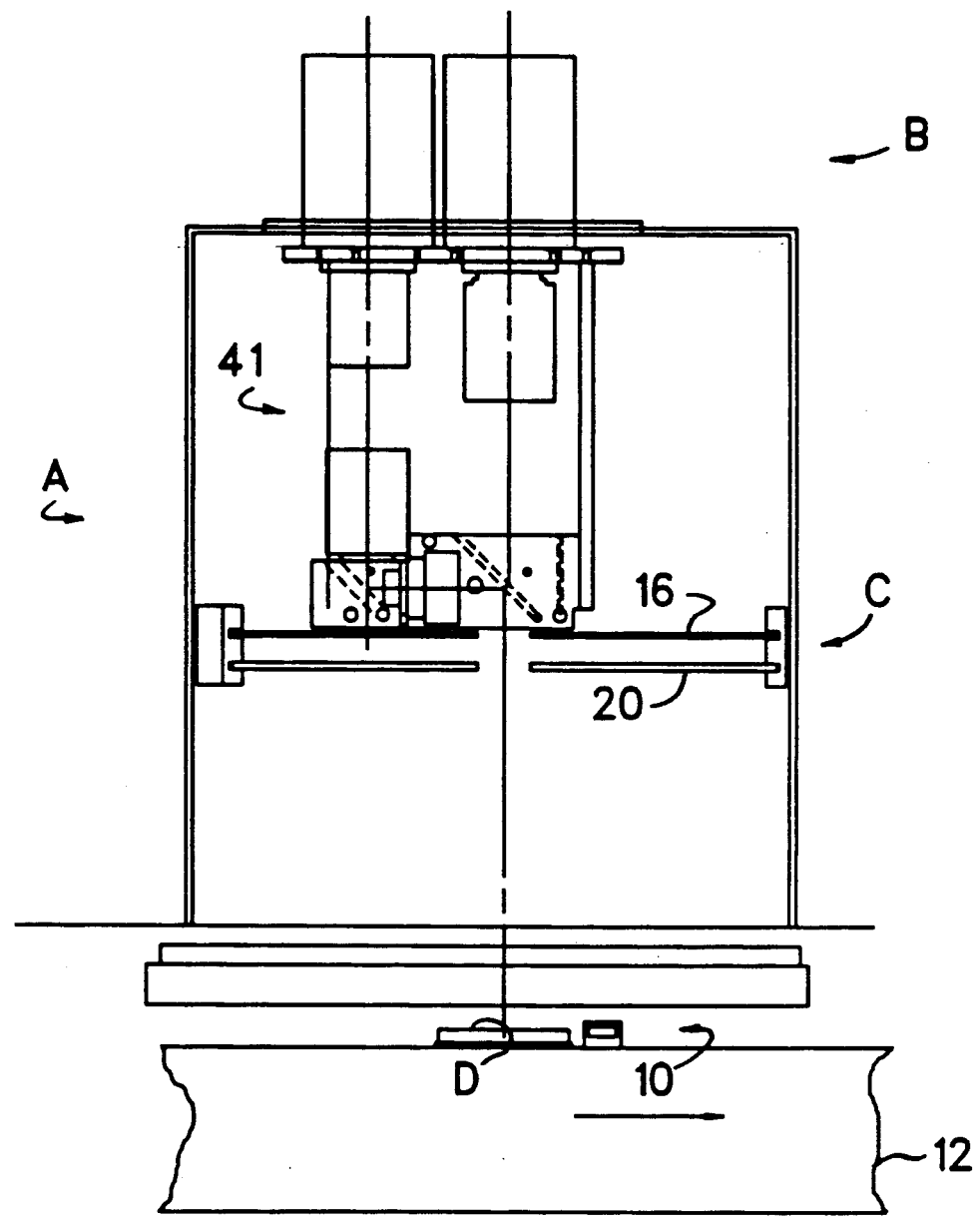
FIG. 1 illustrates a segmented side view of dual-camera video inspection system as employed in the subject invention.

Turning now to the figures, wherein the illustrations are for purposes of describing the preferred embodiment only, and not for the purpose of limiting the same, FIG. 1 illustrates a video inspection system A which includes a camera module B, a lighting unit C, and a specimen D.

In the preferred embodiment, the specimen D is brought to an illumination area 10 by a conveyor belt or means 12. Presence of the specimen D within illumination area 10 is suitably determined by a photo element position sensor, or other suitable tracking mechanism.

When the specimen D is suitably within the illumination area 10, a high-intensity, uniform lighting is provided by the lighting unit C.

Figure 2:
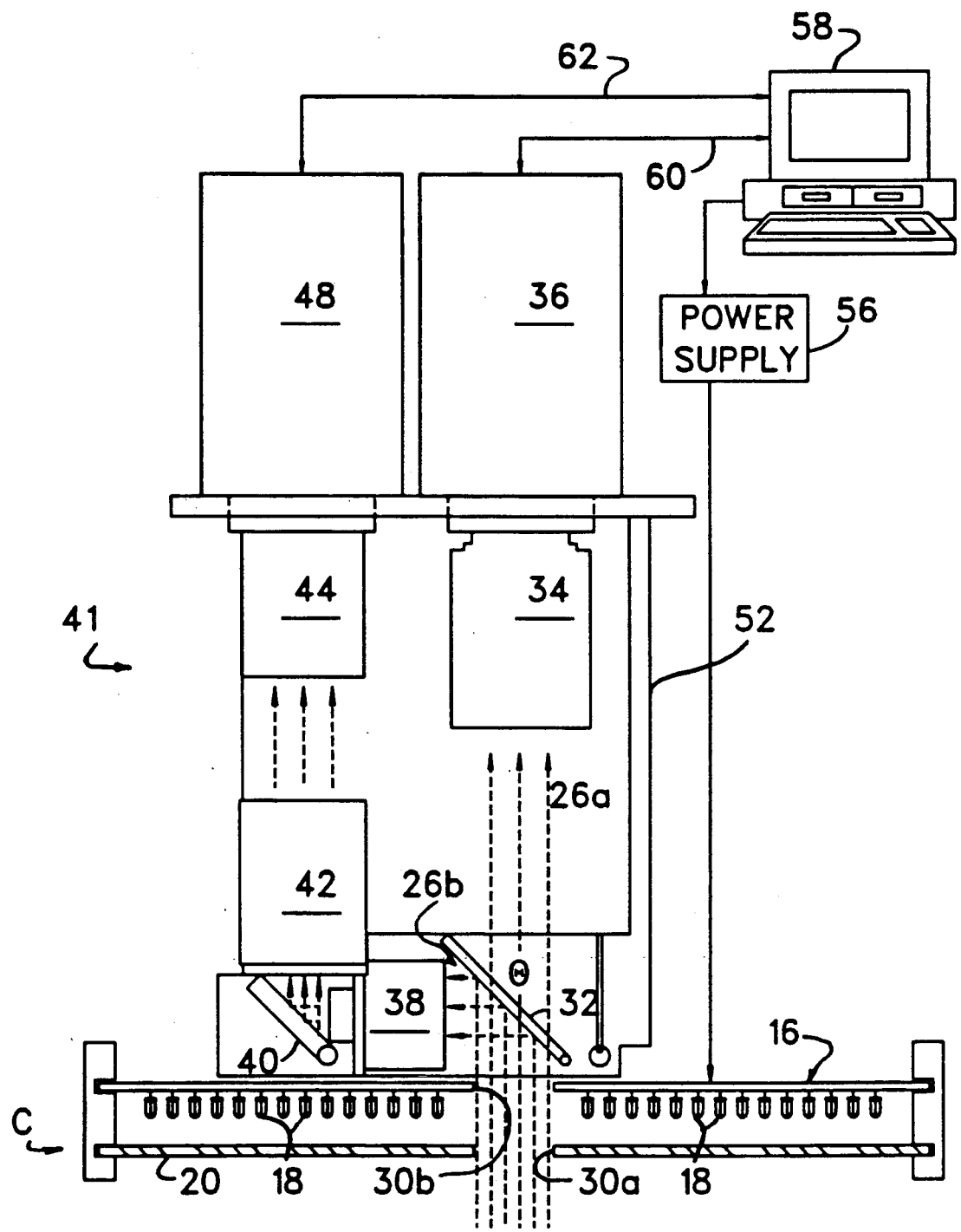
FIG. 2 illustrates, in detail, the dual-camera inspection system and data processor employed in the system FIG. 1.

With continuing reference to FIG. 1, and additional reference to FIG. 2, the lighting unit C which is preferably comprised of an array of solid-state lighting elements 18, which are suitably comprised of focused, light-emitting diodes, or the like. In the illustration of FIG. 2, each of the elements 18 are planarly mounted such that a direction of propagation of light from each element is generally parallel to that of every other element of the array. This particular orientation is suited for illumination of generally planar specimens. Alternatively, formed, such as arcuate, array orientations are often desirable for domed shaped specimens. It will be appreciated that other array orientations are advantageously provided for various specimen shapes.

In the illustration of FIGS. 1 and 2, the plane of light generating elements 18 of array 16 is mounted generally parallel to a generally planar diffuser plate 20. The diffuser plate 20 is suitably comprised of a fine mesh, frosted glass, or the like. The diffuser plate 20 functions to render more uniform light pass therethrough emanating from the light array 16.

Uniform light, from the array 16, is then exposed to the specimen D in the illumination area 10. Light is reflected therefrom, and this reflected light passes through an opening 30, including a diffuser plate portion 30a and an array plate portion 30b. In the preferred embodiment, the portions 30a and 30b are suitably formed of circular openings of a generally equivalent diameter, disposed generally parallely to one another.

Reflected light 26, after passing through opening 30, encounters a partially silvered mirror 32 disposed at an angle $\Theta$ to the direction of propagation of the reflected light 26. With this arrangement, the reflected light 26 is divided into a first portion 26a and a second portion 26b. The degree of silvering of the mirror 32, in addition to the angle $\Theta$ and the relative indices of refraction between the mirror material and the air, dictate the degree to which light will be divided between portions 26a and 26b. The mirror 32 provides, however, a means by which an entire cross-sectional representation of light 26 may be provided to both portion 26a and portion 26b. It will be appreciated that the above-stated factors may also be utilized to vary percentages of intensity afforded to respective portions. In the preferred embodiment, the portion 26a is generally perpendicular to the portion 26b.

Turning initially to the portion 26a of reflected light 26, this portion immediately forms an input to lens 34 of a first video camera 36. It will be appreciated that the afore-described system provides a means by which first and second video images may be acquired from light reflected from a specimen from a single strobe-light like pulse.

Turning now to the portion 26b, the light is presented to a lens apparatus 38 which serves to capture and concentrate the portion 26b to a series of generally-parallel propagating waves. These waves, in turn, reflected from a reflecting means or mirror 40, which in turn redirects the portion 26b to be generally parallel with that portion 26a. Thereafter, the light is presented to a lens array 42 where at the light is focused and parallely directed to a lens 44 of a second video camera 48.

The video cameras 36 and 48 are, in the preferred embodiment, securely mounted by bracket means 52, such that both the first and second video camera and lens array 41, may be reoriented as a contiguous unit. An equilibrium between images generated by portions 26a and 26b of reflected light 26 is thereby maintained.

Light exposed to the cameras 36 and 48 form first and image data portions therewith. Image data generated by each camera 36 and 48 is, in the preferred embodiment, a 512 by 512 pixel array, with each pixel being assigned one of 256 gray scale levels. It will be appreciated that alternative resolutions may be utilized in accordance with desired accuracy, available technology, and acceptable costs.

Image data portions are communicated to a computer or data processor means 58 along data lines 60 and 62 respectively. The data processor 58 serves to acquire data from the video camera 36 and utilize this image data to align image data of the video camera 48 to isolate a selected portion thereof. In addition, the processor 58 is advantageously utilized to trigger lighting elements 18.

Figure 3:
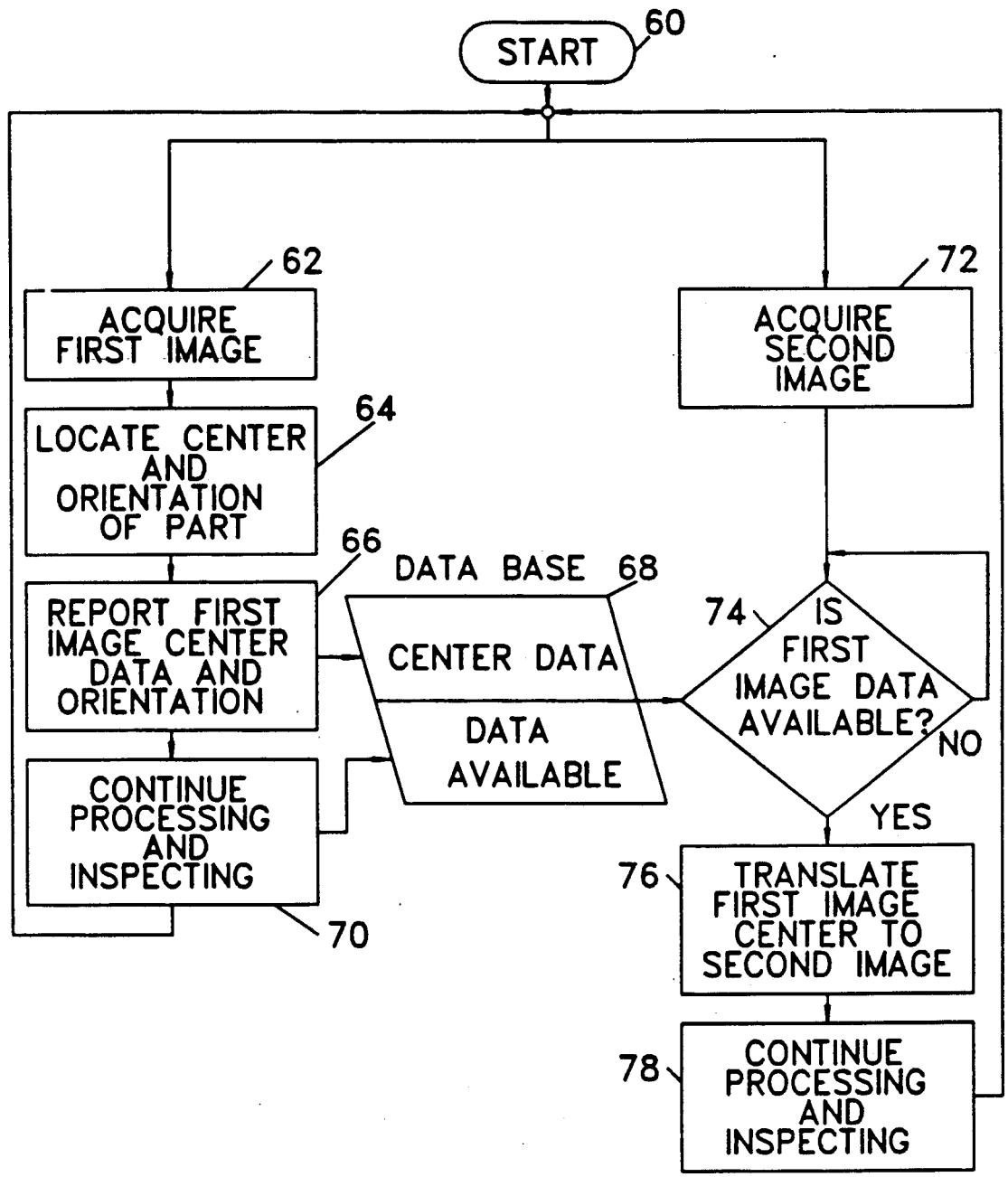
FIG. 3 illustrates, in flow chart form, the procedure for acquiring dual images with an isolated area of a specimen with the apparatus of FIGS. 1 and 2.

Turning now to FIG. 3, operation of the data processor 58 will be described. The action is commenced at start block 60. In block 62, first image data is acquired from the video camera 36. Using this image data, a center of the image, as a whole, is isolated at block 64. This is suitably accomplished by various mathematical means, as will be appreciated by one of ordinary skill in the art. For example, gray scale analysis on resultant image data typically allows for isolation of a well-defined boundary between the specimen under analysis and the background thereto. In the event the specimen is circular or disc-shaped in nature, a selected portion, such as the center, may be isolated by calculating an intersection-point of two unique diameter lines. Additional, suitably mathematical calculations may be accomplished to isolate any desired area of the resultant image.

In the preferred embodiment, the isolated area of interest calculated at block 64 is a central portion of the specimen. This portion presents a critical area in certain applications, such as the above-noted pull tab rivet.

Orientation or image center data isolated at block 64 is communicated to block 66, at which point data is made available to a data base at block 68, and utilized for continued processing at block 70.

Meanwhile, second image data acquired from the video camera 48 is acquired at block 72. This data is retained in a loop at block 74, until such time valid center data is determined to be available at block 68. When such data is available at block 68, processing is passed to block 76, at which point the center data, acquired from the first image, is utilized to isolate a selected portion of the second image data. From this point, processing is passed to block 78, where continued processing occurs.

With the interaction illustrated in the flow chart of FIG. 3, it will be appreciated that the data acquired from the camera 36 is used to orient and isolate data resultant from the camera 42. This provides means by which a critical area of a specimen may be examined.

Figure 4:
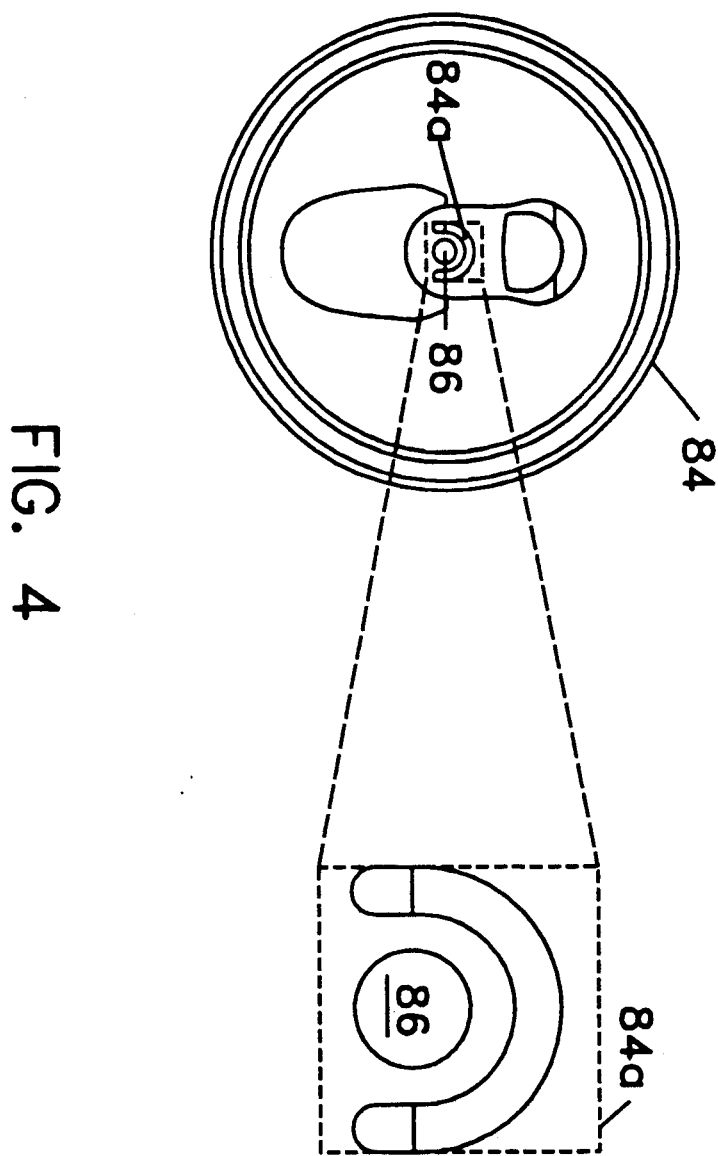
FIG. 4 illustrates a typical specimen for which detailed data of a selected area is advantageously acquired for inspection purposes.

Turning now to FIG. 4, illustrated is a plan view of a soda can lid 84. Although a single, gray scale image of a specimen such as lid 84 renders an extremely thorough inspection possible, the critical area 84a, encompassing an rivet 86, is difficult to inspect given this resolution. The afore-described system provides a means by which the video camera 48 is enabled to isolate a high-resolution image solely of the rivet area 84a. While the video camera 48 suitably forms a set resolution image, for example, 512×512 pixels, of the entire specimen 84, the video camera 42 suitably forms a similar resolution image of the selected area, such as area 84a. This provides a means by which flawed, nicked, or stressed, tabs, or other areas of interest may be afforded special analysis during the inspection process. In addition, processing throughput is maximized and equipment cost is minimized by limiting high resolution data to critical inspection areas.

Upon receipt of first and second image data portions from cameras 36 and 48, the processor 58 comprises the array data to data representative of acceptable image data ranges. Acceptance or rejection of a specimen is then determined in accordance with this data.

The invention has been described with reference to a preferred embodiment. Obviously, modifications and alterations will occur to one of ordinary skill in the art upon a reading and understanding of the specification. It is intended to include all such modifications and alterations insofar as they come within the scope of the appended claims or the equivalents thereof.

Having thus described our invention, it is now claimed:

1. A video inspection apparatus comprising:
   means for receiving light from an associated specimen;
   first and second video camera means for generating image data from light directed thereto;
   apportioning means for providing a first portion of the light to the first video camera means;
   the apportioning means including means for providing a second portion of the light to the second video camera means;
   data processor means for generating alignment data from image data input thereto;
   means for communicating first image data from the first video camera means to the data processor means;
   the processor means including means for isolating a selected portion of image data of the second video camera means in accordance with alignment data generated from the first image data, whereby an isolated image data portion is formed; and
   means for generating second image data from the selected portion of image data of the second video camera means.

2. The video inspection apparatus of claim 1 wherein the apportioning means includes a partially silvered mirror disposed in a path of the light between the associated specimen and the first and second video camera means, whereby one of the first and second portions of the light passes therethrough as a transmitted light portion, and the other of the first and second portions is reflected therefrom as a reflected light portion.

3. The video inspection system of claim 2 further comprising securing means for securing the first and second video camera means such that they are generally directed along parallel axes.

4. The video inspection system of claim 3 further comprising means for determining acceptability of the associated specimen in accordance with at least one of the first image data and the isolated image data.

5. The video inspection system of claim 4 further comprising:
   means for placing the associated specimen in an illumination area; and
   means for directing an array of lighting elements to the illumination area.

6. The video inspection system of claim 5 further comprising means for sensing each of a series of associated specimens in the illumination area.

7. The video inspection system of claim 1 wherein the processor means further includes means for generating the alignment data as representative of a central portion of the associated specimen, and wherein the means for generating second image data includes means for generating a higher resolution image of a central portion of the associated specimen in accordance with the alignment data.

8. A video inspection method comprising the steps of:
   receiving light reflected from an associated specimen;
   providing a first portion of the light to a first video camera;
   generating, in the first video camera, first image data from light received from the associated specimen;
   providing a second portion of the light to a second video camera;
   communicating the first image data from the first video camera to a data processor;
   generating alignment data in the data processor from image data input thereto;
   generating second image data from a selected portion of image data of the second video camera means; and
   isolating a selected portion of the second image data in accordance with alignment data generated from the first image data, whereby an isolated image data portion is formed.

9. The method of claim 8 further comprising the step of separating received light reflected from the associated specimen into the first and second portions, each portion including a cross-sectional representation of generally all the reflected light, such that the first portion has a generally a first selected intensity portion and the second portion has generally a second intensity portion.

10. The method of claim 9 further comprising the step of determining acceptability of the associated specimen in accordance with at least one of the first image data and the isolated image data.

11. The method of claim 10 further comprising the step of placing the associated specimen in an illumination area.

12. The method of claim 11 further comprising the steps of:
   generating the alignment data as representative of a central portion of the associated specimen; and
   generating second image data includes means for generating a higher resolution image of a central portion of the associated specimen in accordance with the alignment data.

13. A video inspection apparatus comprising:
   means for transporting a series of specimens to a inspection field;
   means for determining a presence of a specimen in the inspection field;

energizing means for energizing elements of a lighting array in accordance with a determined presence of the specimen in the inspection field;

means for capturing light of the array after reflection thereof from the specimen;

means for apportioning captured light into first and second light portions;

means for communicating the first light portion to a first video unit, the first video unit including means for generating first image data representative of the first light portion;

means for communicating at least a portion of the first image data to a data processor, the data processor including means for generating alignment data from the first image data;

means for communicating the second light portion to a second video unit, the second video camera including means for generating second image data representative of the second light portion; and means for isolating a selected portion of the second image data in accordance with the alignment data.

14. The video inspection apparatus of claim 13 further comprising:

comparison means for comparing the comparison data with at least one of the first and second image data; and means for determining acceptability of a specimen in accordance with an output of the comparison means.

15. The video inspection apparatus of claim 14 further comprising means for securing the first and second video units to be generally oriented along parallel axes.

16. The video inspection apparatus of claim 15 wherein the lighting array includes a plurality of solid state light emitting elements.

17. The video inspection apparatus of claim 16 further comprising a light diffuser means disposed between the lighting array and the inspection field.

* * * * *